USO11324692B2

United States Patent
Coello et al.

(10) Patent No.: US 11,324,692 B2
(45) Date of Patent: May 10, 2022

(54) METHOD TO PREPARE PHARMACEUTICAL COMPOSITIONS OF SUGGAMADEX

(71) Applicant: Galenicum Health S.L.U., Esplugues de Llobregat (ES)

(72) Inventors: Luis Gomez Coello, Barcelona (ES); Javier Torrejón Nieto, Barcelona (ES)

(73) Assignee: Galenicum Health S.L.U., Esplugues de Llobregat (ES)

( * ) Notice: Subject to any disclaimer, the term of this patent is extended or adjusted under 35 U.S.C. 154(b) by 0 days.

(21) Appl. No.: 16/919,856

(22) Filed: Jul. 2, 2020

(65) Prior Publication Data

US 2021/0000739 A1 Jan. 7, 2021

(30) Foreign Application Priority Data

Jul. 3, 2019 (EP) .................................... 19382569

(51) Int. Cl.
*A61K 9/00* (2006.01)
*A61K 31/724* (2006.01)
*A61L 2/00* (2006.01)
*A61K 9/08* (2006.01)

(52) U.S. Cl.
CPC .......... *A61K 9/0019* (2013.01); *A61K 31/724* (2013.01); *A61L 2/0017* (2013.01); *A61L 2/0023* (2013.01); *A61K 9/08* (2013.01); *A61L 2202/21* (2013.01)

(58) Field of Classification Search
CPC .................................................. A61L 2/0023
See application file for complete search history.

(56) References Cited

U.S. PATENT DOCUMENTS

| 10,494,450 | B2 * | 12/2019 | Alaparthi | ............ C08B 37/0012 |
| 2014/0377185 | A9 * | 12/2014 | Mosher | .............. A61K 49/0447 424/9.43 |
| 2018/0016359 | A1 | 1/2018 | Jia et al. | |
| 2018/0171033 | A1 * | 6/2018 | Alaparthi | ................ A61P 39/02 |

FOREIGN PATENT DOCUMENTS

| EP | 1210090 A2 | 6/2002 |
| WO | 2001/040316 A1 | 6/2001 |
| WO | 2016/194001 A1 | 12/2016 |
| WO | 2017/163165 A1 | 9/2017 |

OTHER PUBLICATIONS

West Pharmaceutical Services, 20mm NovaPure Chlorobutyl 4432/50 Serum Stoppers, publication date (acquired from the webpage source code https://www.westpharma.com/shop/LiquidorSerum%3Dwesteshop_master-liquid%20or%20serum/20mmNovaPureChlorobutyl4432%5B%5BSS%5D%5D50SerumStoppers): May 4, 2006 (Year: 2006).*

* cited by examiner

*Primary Examiner* — Mark V Stevens
*Assistant Examiner* — Alparslan Asan
(74) *Attorney, Agent, or Firm* — Merchant & Gould P.C.; Daniel R. Evans

(57) ABSTRACT

The present invention relates to a method to prepare pharmaceutical compositions of sugammadex, to pharmaceutical compositions of sugammadex and uniform pharmaceutical batches of said compositions.

18 Claims, No Drawings

METHOD TO PREPARE PHARMACEUTICAL COMPOSITIONS OF SUGGAMADEX

This application claims the benefit of the Jul. 3, 2019 filing date of European patent Application No. 19382569.2, which is incorporated herein by reference. To the extent appropriate, a claim of priority is made to the above-disclosed application.

The present invention relates to a method to prepare pharmaceutical compositions of sugammadex, to pharmaceutical compositions of sugammadex and uniform pharmaceutical batches of said compositions.

STATE OF THE ART

Neuromuscular blocking agents are used during the administration of anaesthesia to facilitate endotracheal intubation and to allow surgical access to body cavities, in particular the abdomen and thorax, without hindrance from voluntary or reflex muscle movement. Based on their mechanisms of action, neuromuscular blocking agents are divided into two categories: depolarizing and non-depolarizing.

Non-depolarizing neuromuscular blocking agents compete with acetylcholine for binding to muscle nicotinic acetylcholine receptors; unlike depolarizing neuromuscular agents, they block the activation of the channel by acetylcholine resulting in the softening of the muscles. The more common clinically used neuromuscular blocking agents belong to the non-depolarizing category. These include tubocurarine, atracurium, (cis)atracurium, mivacurium, pancuronium, vecuronium, rocuronium and rapacuronium.

To reverse the neuromuscular block a reversal agent is required, the most common reversal agents are acetylcholinesterase inhibitors. However, acetylcholinesterase inhibitors suffer from selectivity problems that may lead to several side-effects. EP 1 210 090 A1 discloses the use of chemical chelators for its use as reversal agents, mainly cyclic compounds such as cyclic oligosaccharides, cyclophanes, cyclic peptides, calixarenes and crown ethers. The compounds disclosed in EP 1 210 090 A1 show high binding capabilities towards some of the commonly used blocking agents, resulting in effective selective reversal agents.

WO 2001/040316 relates to reversal agents such as 6-mercapto-cyclodextrins, particularly useful to reverse blocking agents such as rocuronium or vecuronium. Among the compounds disclosed in WO 2001/040316, there is 6-Per-deoxy-6-per-(2-carboxyethyl)thio-γ-cyclodextrin also known as sugammadex. Sugammadex is a particularly efficient neuromuscular blockade reversal agent when rocuronium or vecuronium are used as a neuromuscular blocking agent. The empirical formula of sugammadex is $C_{72}H_{112}O_{48}S_8$ and the compound has a molecular weight of 2002.12 g/mol. The structural formula of sugammadex is (I):

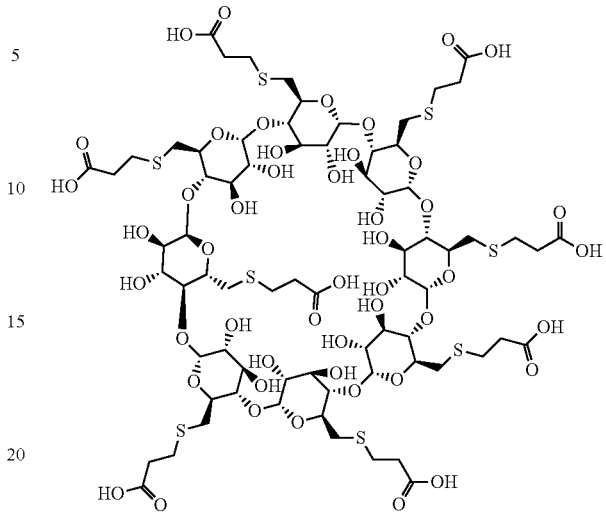

The synthesis of sugammadex molecule involves several steps that can yield several impurities, some with pharmacological activity such as sugammadex monohydroxy. Different processes describing sugammadex synthesis have been disclosed in WO 2001/040316, WO 2016/194001, WO 2017/163165 or US 2018/016359 A1. All these processes need purification steps. Apart from sugammadex monohydroxy, some of the main impurities are sugammadex intramolecular ethers, sugammadex methyl esters and various unidentified impurities. The presence of such impurities tends to have an overall negative effect in the long term stability of the pharmaceutical composition, particularly when subjected to high temperature treatments e.g., sterilization.

Sugammadex is commercialized under the brand Bridion®, an injectable solution of sugammadex sodium salt. However, Bridion® suffers from a relatively high amount of impurities, especially unknown impurities. Unknown impurities are impurities with an unknown structure, as such it's toxicity is unknown and not easily predictable. These unknown impurities can cause a wide variety of side effects, the most grave being life-threatening.

Sodium sugammadex preparations are administered to patients through intravenous injection. Due to the administration route, sugammadex formulations must comply with certain biocompatibility requirements such as aqueous media and regulated pH. However, sugammadex is prone to degradation, especially in aqueous solutions. Therefore, it would be desirable to provide sugammadex aqueous pharmaceutical compositions with low impurity content after being subjected to sterilization processes as well as long term stability.

The present invention aims to overcome the deficiencies and difficulties outlined above. Particularly to provide pharmaceutical compositions with good stability on storage, lower content of impurities after being subjected to sterilization processes and suitable for injection administration as well as the process for manufacturing such pharmaceutical compositions.

SUMMARY OF THE INVENTION

The present invention provides a convenient, easy to scale-up and cost-effective method for preparing sterile aqueous liquid pharmaceutical compositions of sugammadex suitable for injection, having a lower content of impurities, specifically unknown impurities, a clear appearance with acceptable colour and good stability after sterilization and during storage.

The pharmaceutical compositions as disclosed herein are sterile and have a lower amount of impurities, even after prolonged sterilization times, especially the highest unknown impurity G. Also, the sterile pharmaceutical compositions of the present invention can be manufactured under controlled oxygen conditions and, optionally protected from white light providing compositions with lower impurity content and improved stability.

In a first aspect, the present invention relates to a method for preparing an aqueous liquid pharmaceutical composition comprising an active ingredient, wherein the active ingredient is sugammadex, a pharmaceutically acceptable salt of sugammadex or mixtures thereof, wherein the method comprises at least the following steps:
  a) providing a solution, comprising the active ingredient;
  b) if required, adjusting the pH of the solution obtained in step a) from 7 to 8;
  c) filtering the solution obtained in the previous step, preferably through an equal or less than 0.45 μm pore filter;
  d) filling in a suitable pharmaceutical container the solution obtained in the previous step;
  e) terminally sterilizing the solution obtained in the previous step at a temperature from 110° C. to 130° C. during less than 37 min.

In a second aspect, the present invention relates to an aqueous liquid pharmaceutical composition suitable for intravenous administration to a subject comprising an active ingredient, wherein the active ingredient is sugammadex, a pharmaceutically acceptable salt of sugammadex or mixtures thereof, wherein the pharmaceutical composition comprises an effective amount of a pH adjuster to maintain the pH in a range from 7 to 8 and wherein the total amount of impurities is less than 3% (w/w).

In a third aspect, the invention relates to an aqueous liquid pharmaceutical composition comprising an active agent prepared according to the process as herein disclosed.

A fourth aspect of the invention is an aqueous liquid pharmaceutical composition according to the process herein disclosed, wherein the aqueous liquid pharmaceutical composition is packaged in a type I vial with a grey chlorobutyl rubber stopper with a seal.

A fifth aspect of the invention is a pharmaceutical batch of at least 5,000 vials, preferably from 30,000 to 60,000 vials according to the fourth aspect, wherein the sugammadex content or the pharmaceutically acceptable salt thereof content is uniform and/or the vials are stored in a package.

A sixth aspect of the invention is a package which comprises at least one vial according to the fourth aspect comprising a pharmaceutical composition prepared according to the process as herein disclosed.

A seventh aspect of the invention is an aqueous liquid pharmaceutical composition as herein disclosed for its use in the reversal of a neuromuscular block.

DETAILED DESCRIPTION OF THE INVENTION

The present invention provides a method for preparing an aqueous liquid pharmaceutical composition of sugammadex suitable for injection, having good stability after sterilization and on storage. The pharmaceutical compositions, as disclosed herein, have a lower amount of impurities, even after prolonged sterilization times. Also, the pharmaceutical compositions of the present invention can be manufactured under controlled oxygen conditions and, optionally protected from light providing compositions with improved stability.

The term "active agent" as used herein refers to a therapeutically active compound, as well as any prodrugs thereof and pharmaceutically acceptable salts, hydrates and solvates of the compound and the prodrugs.

The term "pH adjuster" as used herein refers to pharmaceutically acceptable excipients which are added to the solution of the active agent to adjust the pH to a certain value. Such pH adjusters can be alkaline or acid agents and may comprise inorganic salts as well as organic acids or salts of organic acids. Additionally, the pH adjusters may be present in the form of a buffer.

The term "pharmaceutically acceptable" as used herein indicates that the substance or composition must be compatible chemically and/or toxicologically, with the other ingredients comprising a formulation, and/or the mammal being treated therewith.

The term "effective" amount as used herein refers to an amount of a compound, agent or substance that is of sufficient quantity to result in a quantifiable effect, e.g., a shift in the pH.

The term "solution" as used herein refers to a liquid preparation of one or more soluble chemical substances, which are dissolved in water.

The term "stable" as used herein refers to a pharmaceutical composition comprising sugammadex wherein the total content of impurities originated from the decomposition of sugammadex does not exceed 3.0% area, preferably 2.0% area, more preferably 1.5% area and most preferably 1.3% area determined by liquid chromatography (HPLC) at 210 nm if such a composition is stored for at least 2 months at 40° C. and 75% relative humidity (RH).

The term "sugammadex sodium" as used herein refers preferably to sugammadex octa sodium salt. As the skilled person would easily recognize, when dissolved in water sugammadex can be present in different protonated forms according to the pH of the solution.

The term "suitable for intravenous administration" as used herein refers to a sterile solution that can be administered intravenously to a patient. Sterility is defined as the absence of living organisms. The conditions of the sterility test are given in the European Pharmacopoeia 9th edition.

The term "suitable pharmaceutical container" as used herein refers to a container for pharmaceutical use is an article which holds or is intended to contain and protect a drug and is or may be in direct contact with it. The container and its closure must not interact physically or chemically with the substance within in any way that would alter its quality.

The term "batch" as used herein refers to a specific quantity of a drug or other material that is intended to have uniform character and quality within specified limits, and is produced according to a single manufacturing order during the same cycle of manufacture. A batch, in the case of a drug product produced by continuous process, is a specific identified amount produced in a unit of time or quantity in a manner that assures it has uniform character and quality within specified limits (Code of Federal Regulations Title 21, Food and Drug Administration Department of Health and Human Services, Subchapter C, Section 210.3 (b) (2) and (10)).

The term "vial" as used herein refers to a vial suitable for containing injectable pharmaceutical compositions according to the European Pharmacopoeia 9th edition, Chapter 3.2.1 "Glass Containers for Pharmaceutical Use".

The term "deoxygenation" as used herein refers to the removal of oxygen in the solution, whether by means of inert gas atmosphere or bubbling inert gas in the solution.

The term "white light" as used herein refers to light with a wavelength below 550 nm.

The term "terminal sterilization" as used herein refers to a process whereby a product is sterilized in its final container or packaging, which permits the measurement and evaluation of quantifiable microbial lethality. The probability of viable microorganisms being present on a product unit after exposure to the proper sterilization process should be less than $10^{-6}$.

The term "thermal sterilization" as used herein refers to a process whereby a product is sterilized using heat. Thermal sterilization uses the thermal lability of a microorganism to prevent its growth.

The term "moist heat sterilization" as used herein refers to a process whereby a product is sterilized using saturated steam). Each product is exposed to direct steam contact at the required temperature and pressure for the specified time. The ideal steam for sterilization is dry saturated steam and entrained water (dryness fraction ≥97%). Pressure serves as a means to obtain the high temperatures necessary to quickly kill microorganisms. Specific temperatures must be obtained to ensure the microbicidal activity.

The term "superheated water spray sterilization" as used herein refers to a process whereby a product is sterilized using water at an appropriate sterilization temperature. The water passes through a heat exchanger to reach appropriate sterilization temperature before it is sprayed onto the product to be sterilized. The elevated flow rate ensures an even temperature throughout the chamber during the sterilization process.

The term "blanketing" as used herein refers to the act of maintaining an inert atmosphere of nitrogen gas ($N_2$) during storage and processing.

The term "unknown impurity G" as used herein refers to the highest impurity of unknown structure with a relative retention time (RRT) of 0.17 min. Percentage of impurity G is determined by HPLC (Column XBridge C8, flow rate 0.7 ml/min, UV detector wavelength 210 nm, column temperature 50° C., mobile phase: phosphate buffer pH 2: ACN with gradient. Mobile phase: 950 ml phosphate buffer pH 2 with 50 ml of acetonitrile, run time 2 h).

The term "bioburden" as used herein refers to the population of viable microorganisms on or in raw materials, products, or labeling/packaging materials determined before sterilization. Bioburden analysis is carried out according to US Pharmacopoeia <71> Sterility tests.

The term "autoclave" as used herein refers to a pressure chamber used to carry out sterilization processes by subjecting them to pressurized saturated steam requiring elevated temperature and pressure different from ambient air pressure.

The terms "0.2 μm pore filter", "0.3 μm pore filter" and "0.45 μm pore filter" as used herein refer to filter where the nominal pore rating have been determined to be 0.2 μm or less, 0.3 or less or 0.45 μm or less according to ISO 13408-2:2018 Aseptic processing of health care products.

The term "effective area" as used herein refers to the area of a filter that is available for filtration for a specific membrane.

All percentages, parts and ratios herein used are by weight unless specifically noted otherwise. As used herein, the term "about" refers preferably to a range that is ±10%, preferably ±5%, or more preferably ±1% of a value with which the term is associated.

Unless otherwise indicated, all the analysis methods are carried out according to the European Pharmacopoeia 9th edition.

In an embodiment of the first aspect of the invention, the solution obtained in step b) is subjected to at least one filtration, preferably at least twice. The term at "least twice" as used herein may refer to at least two filtration steps using different filters or at least to two consecutive filtration steps using the same filter. In another embodiment of the first aspect of the invention, the filtration step produces a sterile solution. Preferably the membrane of the employed filters is made of poly(vinylidene fluoride) or polyethersulfone. Preferably the filters effective area ranges from 100 to 2500 $cm^2$, more preferably from 150 to 2000 $cm^2$, most preferably 200 to 1800 $cm^2$.

Preferably, step e) can be carried out at a temperature from 115° C. to 125° C., preferably from 120° C. to 122° C.

Optionally, step e) can be carried out during 10 min to 31 min, preferably during more than 15 min, more preferably from 15 min to 25 min, more preferably from 15 min to 23 min. Surprisingly, pharmaceutical compositions of sugammadex sodium sterilized under these conditions show a lower amount of impurities and increased stability.

In another embodiment of the first aspect of the invention, step e) can be carried out at a temperature from 115° C. to 125° C., preferably from 120° C. to 122° C. and during 10 min to 31 min, preferably during more than 15 min, more preferably from 15 min to 25 min.

Optionally, step e) can be a thermal sterilization, preferably moist heat sterilization or superheated water spray sterilization, more preferably moist heat sterilization.

Optionally, the solution obtained in step b) can be subjected to filtration using a 0.45 μm pore filter at least twice. Optionally, the solution obtained in step b) can be subjected to filtration at least twice, and least one filtration is through an equal or less than 0.45 μm pore filter and at least one filtration through an equal or less than 0.3 μm pore filter, more preferably through a 0.2 μm pore filter. Optionally, the solution obtained in step b) can be subjected to filtration at least twice, and least one filtration is through a 0.3 μm pore filter, more preferably through a 0.2 μm pore filter. Optionally, the solution obtained in step b) can be subjected to filtration using a 0.2 μm pore filter once, preferably at least twice. In another embodiment of the first aspect of the invention, the bioburden after filtration in step c) is less than 100 CFU/100 mL.

Surprisingly, the present invention provides pharmaceutical compositions with a decreased amount of impurities and improved stability.

In another embodiment of the first aspect of the invention, step (e) is carried out in an autoclave.

A preferred embodiment of the first aspect of the invention is a method for preparing an aqueous liquid pharmaceutical composition comprising an active ingredient, wherein the active ingredient is sugammadex, a pharmaceutically acceptable salt of sugammadex or mixtures thereof, wherein the method comprises at least the following steps:
 a) providing a solution, comprising the active agent;
 b) if required, adjusting the pH of the solution obtained in step a) from 7 to 8;

c) filtering the solution obtained in the previous step, preferably through a equal or less than 0.45 μm pore filter;
d) filling in a suitable pharmaceutical container the solution obtained in the previous step;
e) terminally sterilizing of the solution obtained in step d) at a temperature from 110° C. to 130° C. during less than 37 min;

wherein step c) is performed at least twice, wherein the sterilization temperature in step e) is from 115° C. to 125° C., preferably from 120° C. to 122° C. and the sterilization time in step e) is more than 15 min, preferably from 17 min to 23 min. The inventors have found that pharmaceutical compositions of sugammadex sodium subjected to a filtration allow shorter sterilization times while maintaining the sterility of the pharmaceutical composition. Hence resulting in pharmaceutical compositions with a lower amount of impurities and increased stability.

A preferred embodiment of the first aspect of the invention is a method for preparing an aqueous liquid pharmaceutical composition comprising an active ingredient, wherein the active ingredient is sugammadex, a pharmaceutically acceptable salt of sugammadex or mixtures thereof, wherein the method comprises at least the following steps:
a) providing a solution, comprising the active agent;
b) if required, adjusting the pH of the solution obtained in step a) from 7 to 8;
c) filtering the solution obtained in the previous step, preferably through a equal or less than 0.45 μm pore filter;
d) filling in a suitable pharmaceutical container the solution obtained in the previous step;
e) terminally sterilizing of the solution obtained in step d) at a temperature from 110° C. to 130° C. during less than 37 min;

wherein the step c) is performed at least twice, and least one filtration is through an equal or less than 0.45 μm pore filter and/or at least one filtration through an equal or less than 0.3 μm pore filter, preferably through a 0.2 μm pore filter, wherein the sterilization temperature in step e) is from 115° C. to 125° C., preferably from 120° C. to 122° C. and the sterilization time in step e) is more than 15 min, preferably from 15 min to 25 min, more preferably from 17 min to 23 min. The inventors have found that pharmaceutical compositions of sugammadex sodium subjected to a filtration allow shorter sterilization times while maintaining the sterility of the pharmaceutical composition. Hence resulting in pharmaceutical compositions with a lower amount of impurities and increased stability.

A preferred embodiment of the first aspect of the invention is a method for preparing an aqueous liquid pharmaceutical composition comprising an active ingredient, wherein the active ingredient is sugammadex, a pharmaceutically acceptable salt of sugammadex or mixtures thereof, wherein the method comprises at least the following steps:
a) providing a solution, comprising the active agent;
b) if required, adjusting the pH of the solution obtained in step a) from 7 to 8;
c) optionally, filtering the solution obtained in the previous step through a 0.2 μm pore filter;
d) filling in a suitable pharmaceutical container the solution obtained in the previous step;
e) terminally sterilizing of the solution obtained in step d) at a temperature from 110° C. to 130° C. during less than 37 min;

wherein step c) is performed at least once, preferably at least twice, wherein the sterilization temperature in step e) is from 115° C. to 125° C., preferably from 120° C. to 122° C. and the sterilization time in step e) is more than 15 min, preferably from 15 min to 25 min, more preferably from 17 min to 23 min. The inventors have found that pharmaceutical compositions of sugammadex sodium subjected to a filtration allow shorter sterilization times while maintaining the sterility of the pharmaceutical composition. Hence resulting in pharmaceutical compositions with a lower amount of impurities and increased stability.

In an embodiment of the first aspect of the invention, the active agent of the solution of step a) is sugammadex, preferably the active agent is sugammadex sodium. In another embodiment, the solution comprises a total amount of active ingredient, measured as free acid, of about 50 to about 150 mg/mL, preferably the total amount of active agent is about 75 to about 125 mg/mL, more preferably the total amount of active agent is about 90 to about 110 mg/mL.

In another embodiment of the first aspect of the invention, the pH in step b) is adjusted to a range from about 7.2 to about 7.8, preferably about 7.4 to about 7.6, more preferably about 7.5.

In another embodiment of the first aspect of the invention, the pH adjusters used in step b) are selected from HCl, NaOH, KOH, CaOH, acetic acid, ascorbic acid, citric acid, phosphate salts, or mixtures thereof, preferably HCl or NaOH. In another embodiment, the concentration of the pH adjuster is about 0.01 N to about 1N.

In another embodiment of the first aspect of the invention, the method comprises a step of deoxygenation. In another embodiment, the deoxygenation is achieved by bubbling the solution comprising the active ingredient with an inert gas, preferably the inert gas used for bubbling is nitrogen. In another embodiment, the oxygen content of the aqueous liquid pharmaceutical composition is below 5 ppm, preferably below 2 ppm. Surprisingly, pharmaceutical compositions of sugammadex sodium with low oxygen content show increased stability.

Optionally, the pharmaceutically suitable container comprising the aqueous liquid pharmaceutical composition can be blanketed with an inert gas in step d), preferably the inert topping gas heavier than air. In a preferred embodiment, the inert topping gas is nitrogen. Optionally, the pharmaceutically suitable container can be cleared of the air contained therein, by insufflation with an inert gas, preferably the inert gas is nitrogen.

The method disclosed herein is a robust method that produces sterilized pharmaceutical compositions with reduced amount of impurities and increased stability even when residual solvents are present, e.g., 1.0% to 2.5% (w/w) EtOH.

In another embodiment of the first aspect of the invention, the aqueous liquid pharmaceutical compositions obtained with the method disclosed have a total amount of impurities less than 3% (w/w), preferably less than 2% (w/w), more preferably less than 1.5% (w/w), most preferably 1.3% (w/w). In another embodiment of the first aspect of the invention, the aqueous liquid pharmaceutical compositions obtained with the method disclosed have an amount of unknown impurity G lower than about 0.25% (w/w), preferably equal or less than about 0.20 (w/w). Surprisingly, pharmaceutical compositions of sugammadex sodium, prepared according to the present invention, show a lower amount of total impurities and unknown impurity G. In contrast, Bridion® shows a higher content of unknown impurities.

Another preferred embodiment of the first invention is a method for preparing an aqueous liquid pharmaceutical composition comprising an active ingredient, wherein the active ingredient is sugammadex, a pharmaceutically acceptable salt of sugammadex or mixtures thereof wherein the method comprises at least the following steps:
a) providing a solution, comprising the active ingredient;
b) if required, adjusting the pH of the solution obtained in step a) from 7 to 8;
c) optionally, filtering the solution obtained in the previous step through a 0.2 μm pore filter;
d) filling in a suitable pharmaceutical container the solution obtained in the previous step;
e) terminally sterilizing the solution obtained in step d). wherein the pH in step c) is adjusted to a range from about 7.2 to about 7.8, preferably about 7.4 to about 7.6, more preferably about 7.5, wherein the pharmaceutical compositions obtained have a total amount of impurities less than 3% (w/w), preferably less than 2 (w/w), more preferably less than 1.5% (w/w), most preferably less than 1.3% (w/w), wherein step c) is performed at least once, preferably at least twice, wherein the sterilization temperature in step e) is from 115° C. to 125° C., preferably from 120° C. to 122° C. and the sterilization time in step e) is more than 15 min, preferably from 15 min to 25 min, more preferably from 17 min to 23 min. The inventors have found that pharmaceutical compositions of sugammadex sodium subjected to this sterilization conditions show a lower amount of impurities and increased stability.

Another preferred embodiment of the first aspect of the invention is a method for preparing an aqueous liquid pharmaceutical composition comprising an active ingredient, wherein the active ingredient is sugammadex, a pharmaceutically acceptable salt of sugammadex or mixtures thereof, wherein the method comprises at least the following steps:
a) providing a solution, comprising sugammadex,
b) if required, adjusting the pH of the solution obtained in step a) from 7.0 to 8.0,
c) optionally, filtering the solution obtained in step b) through a 0.2 μm pore filter,
d) filling a suitable pharmaceutical container with the solution obtained in step c),
e) terminally sterilizing the solution obtained in step d);
wherein the pH in step b) is adjusted to a range from about 7.2 to about 7.8, preferably about 7.4 to about 7.6, more preferably about 7.5, wherein step c) is performed at least once, preferably at least twice, wherein the sterilization temperature in step e) is from 115° C. to 125° C., preferably from 120° C. to 122° C. and the sterilization time in step e) is more than 15 min, preferably from 15 min to 25 min, more preferably from 17 min to 23 min.

In another embodiment of the first aspect, the manufactured pharmaceutical compositions are suitable for parenteral administration, preferably intravenous injection.

In an embodiment of the second aspect of the present invention, the aqueous liquid pharmaceutical composition has a pH in a range from about 7.2 to about 7.8, preferably about 7.4 to about 7.6.

In another embodiment of the second aspect of the present invention, the aqueous liquid pharmaceutical composition has a total amount of impurities less than 3% (w/w), preferably less than 2% (w/w), more preferably less than 1.5% (w/w), most preferably less than 1.3% (w/w).

In another embodiment of the second aspect, the aqueous liquid pharmaceutical composition comprises a total amount of active ingredient, measured as free acid, of about 50 mg/mL to about 150 mg/mL, preferably the total amount of active agent is about 75 mg/mL to about 125 mg/mL, more preferably the total amount of active agent is about 90 mg/mL to about 110 mg/mL.

In a preferred embodiment, the active agent is sugammadex sodium.

In another embodiment of the second aspect, the pharmaceutical composition has an amount of unknown impurity G lower than about 0.25% (w/w), preferably equal or less than about 0.20% (w/w). Surprisingly, pharmaceutical compositions of sugammadex sodium with an amount of impurities as indicated show increased stability.

In another embodiment of the second aspect, the pH adjusters of the aqueous liquid pharmaceutical composition are selected from HCl, NaOH, KOH, CaOH, acetic acid, ascorbic acid, citric acid, phosphate salts, or mixtures thereof, preferably HCl or NaOH. In another embodiment the concentration of the pH adjuster is about 0.01 N to about 1 N.

In another embodiment of the second aspect, the aqueous liquid pharmaceutical composition has a pH in a range from about 7.2 to about 7.8, preferably about 7.4 to about 7.6 and a total amount of impurities less than 3% (w/w), more preferably less than 2% (w/w), even more preferably less than 1.5% (w/w), most preferably 1.3% (w/w).

In another embodiment of the second aspect, the aqueous liquid pharmaceutical composition has an oxygen content less than 5 ppm, preferably less than 2 ppm.

In another embodiment of the second aspect, the aqueous liquid pharmaceutical composition has a pH in a range from about 7.2 to about 7.4, preferably about 7.4 to about 7.6, wherein the total amount of impurities is less than 3% (w/w), preferably less than 2% (w/w), more preferably less than 2.5% (w/w), most preferably 1.3% (w/w).

In another embodiment of the second aspect, the pharmaceutical composition is sterile. In another embodiment of the second aspect, the pharmaceutical composition is sterilized in an autoclave.

In another embodiment of the second aspect, the pharmaceutical composition is suitable for parenteral administration, preferably intravenous injection.

In a third aspect, the invention relates to an aqueous liquid pharmaceutical composition prepared according to the first aspect of the invention.

In an embodiment of the fourth aspect of the invention, the pharmaceutically suitable container is a vial, preferably a type I vial with a grey chlorobutyl rubber stopper, with a seal. In another embodiment of the fourth aspect of the invention, the vial comprises about 2 mL or about 5 mL of an aqueous liquid pharmaceutical composition comprising the active agent.

Preferably, the package is in the form of a cardboard box. In another embodiment of the sixth aspect, the package further comprises at least one vial comprising a neuromuscular blocking agent, preferably the neuromuscular blocking agent is rocuronium or vecuronium.

Further aspects and embodiments of the present invention can be found in the following numbered clauses:

Clause 1. A method for preparing an aqueous liquid pharmaceutical composition comprising an active ingredient, wherein the active ingredient is sugammadex, a pharmaceutically acceptable salt of sugammadex or mixtures thereof, wherein the method comprises at least the following steps:
a) providing a solution, comprising the active ingredient;
b) if required, adjusting the pH of the solution obtained in the previous step from 7 to 8;

c) filtering the solution obtained in the previous step through a equal or less 0.45 than μm pore filter;

d) filling a suitable pharmaceutical container with the solution obtained in the previous step;

e) terminally sterilizing the solution obtained in step d) at a temperature from 110° C. to 130° C. during less than 37 min.

Clause 2. A method for preparing an aqueous liquid pharmaceutical composition comprising an active ingredient, wherein the active ingredient is sugammadex, a pharmaceutically acceptable salt of sugammadex or mixtures thereof, wherein the method comprises at least the following steps:

a) providing a solution, comprising the active ingredient;

b) if required, adjusting the pH of the solution obtained in the previous step from 7 to 8;

c) optionally, filtering the solution obtained in the previous step through a 0.2 μm pore filter;

d) filling a suitable pharmaceutical container with the solution obtained in the previous step;

e) terminally sterilizing the solution obtained in step d) at a temperature from 110° C. to 130° C. during less than 37 min.

Clause 3. The method according to any one of the preceding clauses, wherein the step c) is performed at least twice, and least one filtration is through an equal or less than 0.45 μm pore filter and/or at least one filtration through an equal or less than 0.3 μm pore filter, preferably through a 0.2 μm pore filter.

Clause 4. The method according to any one of the preceding clauses, wherein step e) is carried out at a temperature from 115° C. to 125° C., preferably from 120° C. to 122° C.

Clause 5. The method according to any one of the preceding clauses, wherein step e) is carried out during 10 min to 31 min, preferably during more than 15 min, more preferably from 15 min to 25 min.

Clause 6. The method according to any one of the preceding clauses, wherein step e) is carried out at a temperature from 115° C. to 125° C., preferably from 120° C. to 122° C. and during 10 min to 31 min, preferably during more than 15 min, more preferably from 15 min to 25 min.

Clause 7. The method according to any one of the preceding clauses, wherein the terminal sterilization of step e) is a thermal sterilization, preferably moist heat sterilization or superheated water spray sterilization, more preferably moist heat sterilization.

Clause 8. The method according to any one of the preceding clauses, wherein step e) is carried out at a temperature from 115° C. to 125° C., preferably from 120° C. to 122° C. and during 10 min to 31 min, preferably during more than 15, more preferably from 15 min to 25 min, most preferably from 15 min to 23 min.

Clause 9. The method according to any one of the preceding clauses, wherein the solution bioburden after step c) is less than 100 CFU/100 mL.

Clause 10. The method according to any one of the preceding claims, wherein step e) is carried out in an autoclave.

Clause 11. The method according to any one of the preceding clauses, wherein step c) is performed at least once, preferably at least twice, wherein the sterilization temperature in step e) is from 115° C. to 125° C. and the sterilization time in step e) from 15 min to 25 min, more preferably the sterilization temperature is from 120 to 122° C. and the sterilization time more than 15 min, more preferably the sterilization temperature is from 120 to 122° C. and the sterilization time from 17 min to 23 min.

Clause 12. The method according to any one of the preceding clauses, wherein the active ingredient is sugammadex sodium.

Clause 13. The method according to any one of the preceding clauses, wherein the total amount of active ingredient in the pharmaceutical composition, measured as free acid, is about 50 mg/mL to about 150 mg/mL, preferably the total amount of sugammadex is about 75 mg/mL to about 125 mg/mL, more preferably the total amount of sugammadex is about 90 mg/mL to about 110 mg/mL.

Clause 14. The method according to any one of the preceding clauses, wherein the pH is adjusted with a pH adjuster selected from HCl, NaOH, KOH, CaOH, acetic acid, ascorbic acid, citric acid, phosphate salts, or mixtures thereof, preferably HCl or NaOH.

Clause 15. The method according to any one of the preceding clauses, wherein the concentration of the pH adjuster is about 0.01 N to about 1N.

Clause 16. The method according to any one of the preceding clauses, wherein the pH in the aqueous liquid pharmaceutical composition is about 7.2 to about 7.8, preferably about 7.4 to about 7.6, more preferably about 7.5.

Clause 17. The method according to any one of the preceding clauses, comprising a step of deoxygenation.

Clause 18. The method according to any one of the preceding clauses, wherein the deoxygenation is achieved by bubbling the solution comprising the active ingredient with an inert gas.

Clause 19. The method according to any one of the preceding clauses, wherein the inert gas is nitrogen.

Clause 20. The method according to any one of the preceding clauses, wherein the oxygen content of the aqueous liquid pharmaceutical composition is below 2 ppm.

Clause 21. An aqueous liquid pharmaceutical composition suitable for intravenous administration to a subject comprising an active ingredient, wherein the active ingredient is sugammadex, a pharmaceutically acceptable salt of sugammadex or mixtures thereof, wherein the pharmaceutical composition comprises an effective amount of a pH adjuster to maintain the pH in a range from 7 to 8 and wherein the total amount of impurities is less than 3% (w/w).

Clause 22. The aqueous liquid pharmaceutical composition according to the preceding clause, wherein the pharmaceutical composition has a pH in a range from about 7.2 to about 7.8, preferably about 7.4 to about 7.6.

Clause 23. The aqueous liquid pharmaceutical composition according to the two preceding clauses, wherein the total amount of impurities is less than 1.5% (w/w), preferably less than 1.3% (w/w).

Clause 24. The aqueous liquid pharmaceutical composition according to the three preceding clauses, wherein the total amount of active ingredient measured as a free acid is about 50 mg/mL to about 150 mg/mL, preferably the total amount of sugammadex is about 75 mg/mL to about 125 mg/mL, more preferably the total amount of sugammadex is about 90 mg/mL to about 110 mg/mL.

Clause 25. The aqueous liquid pharmaceutical composition of according to the four preceding clauses, wherein the amount of individual unknown impurity G is less than about 0.25% (w/w), preferably the amount of unknown impurity G is equal or less than about 0.20% (w/w).

Clause 26. The aqueous liquid pharmaceutical composition according to the five preceding clauses, wherein the oxygen content of the pharmaceutical composition is below 2 ppm.

Clause 27. The aqueous liquid pharmaceutical composition according to the six preceding clauses, wherein such composition is sterile.

Clause 28. An aqueous liquid pharmaceutical composition comprising an active agent prepared according to any of the 5 preceding clauses 1 to 18.

Clause 29. The aqueous liquid pharmaceutical composition of any of the eight preceding clauses, wherein the aqueous liquid pharmaceutical composition is packaged in a type I vial with a grey chlorobutyl rubber stopper, with a seal.

Clause 30. A pharmaceutical batch comprising at least 5,000, preferably from 30,000 to 60,000 vials as defined in any of the preceding clauses.

Clause 31. A cardboard box package comprising at least 1 vial according to any of the preceding clauses.

Clause 32. A cardboard box package comprising at least 1 vial according to clause 27 further comprising a vial comprising a neuromuscular blocking agent, preferably the neuromuscular blocking agent is rocuronium or vecuronium.

Clause 33. The aqueous liquid pharmaceutical composition according to any of the preceding clauses for its use as a reversal agent for drug-induced neuromuscular block.

Clause 34. The aqueous liquid pharmaceutical composition according to any of the preceding clauses for its use as a reversal agent for drug-induced neuromuscular block wherein the neuromuscular block is induced by rocuronium or vecuronium.

EXAMPLES

Example 1. Preparation of the Aqueous Liquid Pharmaceutical Compositions

The aqueous liquid pharmaceutical composition was prepared as follows:
A. Procedure of weighing and sampling sugammadex sodium
 1. Transfer sugammadex sodium API to a controlled area and weigh the sugammadex sodium according to the formula (108.8 mg).
B. Preparation of the solution
 1. Add the needed water for injection in a compounding vessel and bubble with filtered nitrogen gas.
 2. Add the total amount of sugammadex sodium into the vessel under stirring until the total dissolution of the API.
 3. Adjust the pH of the solution with hydrochloric acid 0.1 N and/or sodium hydroxide 0.1 N to pH target of 7.5.
 4. Stop nitrogen bubbling and make up to the final volume with water for injection (100 mL).
 5. Restart the filtered nitrogen bubbling and stir the solution.
 6. Filter the solution twice through a 0.2 µm pore filter.
C. Filling of the vials
 1. Fill the active solution into cleaned, sterilized and pyrogenic free glass vials.
 2. Flush nitrogen inside the vials in order to obtain a nitrogen blanket and close the vials with the stoppers and seal the vials with the flip-off caps.
D. Terminal sterilization
 1. Expose the product at 121° C. for 15 minutes in order to sterilize it.

Terminal sterilization was carried in an autoclave (Telstar SM7710) with a chamber volume of 490 L. See sterilization process print out (table 1).

TABLE 1

Print out of the sterilization process parameters.

| Time | Temperature (° C.) | | | | | | Pressure (kPa) | |
| --- | --- | --- | --- | --- | --- | --- | --- | --- |
| | T-Con | T-Cha | T-Pro | T-HE | T-Fil | T-Air | P-Cha | P-Jac |
| 15:05:53 | 31.3 | 62.5 | 25.6 | 28.7 | 28.6 | 28.4 | 98.8 | 98.4 |
| 15:06:00 | 31.3 | 62.5 | 25.5 | 28.7 | 28.6 | 28.4 | 98.9 | 105.4 |
| 15:07:00 | 31.3 | 62.4 | 25.2 | 28.7 | 28.6 | 28.3 | 100.0 | 147.1 |
| 15:08:00 | 31.2 | 63.2 | 24.9 | 28.7 | 28.6 | 28.3 | 101.2 | 200.2 |
| 15:09:00 | 31.1 | 64.8 | 24.8 | 28.7 | 28.6 | 28.3 | 102.8 | 177.5 |
| 15:09:44 | 31.1 | 66.4 | 24.7 | 28.7 | 28.6 | 28.2 | 104.1 | 204.1 |
| 15:09:45 | 31.1 | 66.5 | 24.7 | 28.7 | 28.6 | 28.2 | 104.1 | 205.2 |
| 15:10:00 | 32.1 | 67.0 | 24.7 | 28.7 | 28.6 | 28.2 | 76.3 | 205.0 |
| 15:11:00 | 36.0 | 68.9 | 24.6 | 28.7 | 28.5 | 28.2 | 20.3 | 204.5 |
| 15:11:01 | 36.0 | 68.9 | 24.6 | 28.7 | 28.5 | 28.2 | 19.9 | 203.6 |
| 15:12:00 | 87.6 | 88.9 | 28.9 | 28.7 | 28.5 | 28.2 | 81.9 | 202.8 |
| 15:12:08 | 91.2 | 92.0 | 34.3 | 28.7 | 28.5 | 28.2 | 90.9 | 203.1 |
| 15:13:00 | 80.3 | 81.5 | 70.4 | 28.7 | 28.5 | 28.1 | 45.8 | 202.8 |
| 15:14:00 | 64.7 | 75.9 | 67.9 | 28.7 | 28.5 | 28.1 | 21.1 | 204.0 |
| 15:14:05 | 60.4 | 75.8 | 67.2 | 28.7 | 28.5 | 28.1 | 19.9 | 204.2 |
| 15:14:59 | 95.1 | 95.3 | 83.7 | 28.6 | 28.5 | 28.1 | 90.9 | 204.7 |
| 15:15:00 | 95.1 | 95.3 | 83.7 | 28.6 | 28.5 | 28.1 | 90.9 | 204.7 |
| 15:16:00 | 78.2 | 81.0 | 85.7 | 28.7 | 28.5 | 28.1 | 41.9 | 203.1 |
| 15:16:56 | 60.7 | 78.2 | 77.0 | 28.6 | 28.5 | 28.1 | 19.9 | 206.4 |
| 15:17:00 | 60.4 | 78.2 | 76.5 | 28.6 | 28.5 | 28.1 | 25.5 | 206.4 |
| 15:18:00 | 101.1 | 101.2 | 94.0 | 28.6 | 28.5 | 28.2 | 110.8 | 203.9 |
| 15:19:00 | 117.4 | 117.5 | 111.3 | 28.6 | 28.5 | 32.1 | 187.8 | 205.7 |
| 15:20:00 | 121.6 | 121.4 | 120.0 | 28.6 | 28.5 | 40.3 | 206.4 | 205.4 |
| 15:20:46 | 121.6 | 121.4 | 121.0 | 28.6 | 28.5 | 41.0 | 206.3 | 204.4 |
| 15:21:00 | 121.6 | 121.4 | 121.0 | 28.6 | 28.5 | 41.2 | 206.3 | 204.3 |
| 15:22:00 | 121.5 | 121.4 | 121.2 | 28.6 | 28.5 | 42.1 | 206.1 | 204.4 |
| 15:23:00 | 121.6 | 121.4 | 121.3 | 28.6 | 28.6 | 42.7 | 205.9 | 204.5 |
| 15:24:00 | 121.6 | 121.4 | 121.2 | 28.6 | 28.6 | 43.6 | 205.8 | 205.9 |
| 15:25:00 | 121.6 | 121.4 | 121.2 | 28.7 | 28.6 | 44.2 | 205.6 | 205.8 |
| 15:26:00 | 121.5 | 121.4 | 121.2 | 28.7 | 28.6 | 44.5 | 205.6 | 206.1 |
| 15:27:00 | 121.5 | 121.4 | 121.3 | 28.7 | 28.6 | 45.0 | 205.5 | 204.2 |
| 15:28:00 | 121.6 | 121.4 | 121.2 | 28.7 | 28.7 | 45.4 | 205.5 | 205.2 |
| 15:29:00 | 121.6 | 121.4 | 121.3 | 28.7 | 28.7 | 46.3 | 205.4 | 205.4 |
| 15:30:00 | 121.6 | 121.4 | 121.3 | 28.7 | 28.7 | 46.4 | 205.6 | 205.8 |
| 15:31:00 | 121.5 | 121.4 | 121.3 | 28.7 | 28.8 | 46.7 | 205.5 | 205.0 |
| 15:32:00 | 121.6 | 121.4 | 121.3 | 28.7 | 28.8 | 47.0 | 205.3 | 204.9 |
| 15:33:00 | 121.5 | 121.4 | 121.2 | 28.7 | 28.8 | 47.1 | 205.1 | 204.5 |
| 15:33:51 | 121.5 | 121.4 | 121.2 | 28.8 | 28.9 | 47.9 | 205.2 | 206.6 |
| 15:34:00 | 121.6 | 121.2 | 121.2 | 28.7 | 28.9 | 48.0 | 205.2 | 191.3 |
| 15:35:00 | 91.2 | 112.1 | 112.1 | 28.8 | 29.0 | 45.6 | 209.4 | 123.0 |
| 15:35:55 | 78.7 | 106.2 | 106.2 | 28.8 | 29.0 | 44.0 | 128.0 | 102.7 |
| 15:36:00 | 76.1 | 105.8 | 105.8 | 28.8 | 29.0 | 43.9 | 110.2 | 101.5 |
| 15:37:00 | 80.9 | 102.3 | 102.3 | 28.8 | 28.6 | 43.0 | 108.0 | 101.9 |
| 15:37:36 | 86.1 | 99.9 | 99.9 | 28.8 | 28.4 | 42.8 | 107.7 | 99.7 |
| 15:38:00 | 86.0 | 98.6 | 98.6 | 28.8 | 28.2 | 42.5 | 106.5 | 98.1 |
| 15:39:00 | 84.4 | 95.2 | 95.2 | 28.9 | 28.2 | 42.0 | 150.0 | 98.1 |
| 15:40:00 | 83.4 | 90.0 | 92.3 | 28.9 | 28.3 | 41.6 | 133.4 | 98.0 |
| 15:41:00 | 82.3 | 88.1 | 90.0 | 28.9 | 28.4 | 41.3 | 131.2 | 98.0 |
| 15:42:00 | 81.0 | 86.6 | 88.1 | 28.9 | 28.6 | 41.1 | 129.9 | 98.0 |
| 15:43:00 | 79.6 | 85.3 | 86.6 | 28.9 | 28.7 | 40.8 | 128.8 | 98.0 |
| 15:44:00 | 78.0 | 84.1 | 85.3 | 29.0 | 28.8 | 40.5 | 128.1 | 98.0 |
| 15:45:00 | 76.3 | 82.9 | 84.1 | 29.0 | 28.9 | 40.3 | 127.5 | 97.9 |
| 15:46:00 | 74.7 | 81.8 | 82.9 | 29.0 | 28.9 | 40.0 | 126.9 | 98.0 |
| 15:47:00 | 73.0 | 80.9 | 81.8 | 29.0 | 29.0 | 39.8 | 126.6 | 98.1 |
| 15:48:00 | 71.3 | 80.0 | 80.9 | 29.0 | 29.1 | 39.5 | 126.1 | 98.1 |
| 15:48:54 | 69.9 | 80.0 | 80.0 | 29.1 | 29.1 | 39.3 | 125.8 | 98.1 |
| 15:49:00 | 69.7 | 79.6 | 80.0 | 29.1 | 29.1 | 39.3 | 125.7 | 98.1 |
| 15:49:24 | 69.1 | 75.9 | 79.6 | 29.1 | 29.1 | 39.2 | 127.4 | 103.3 |
| 15:50:00 | 68.1 | 76.3 | 79.1 | 29.1 | 29.2 | 39.1 | 104.0 | 98.2 |

Example 2. Manufacturing Conditions: $N_2$ and White Light

Example 1 formulation was prepared under presence/absence of $N_2$ bubbling, white light and blanketing the content of the vial with $N_2$. Table 2 shows the different conditions used in examples 2.1 to 2.5.

TABLE 2

| Preparation conditions. | | | | | |
| --- | --- | --- | --- | --- | --- |
| | Ex. 2.1 | Ex. 2.2 | Ex. 2.3 | Ex. 2.4 | Ex. 2.5 |
| $N_2$ bubbling | NO | YES | YES | NO | YES |
| $N_2$ blanketing | NO | NO | NO | NO | YES |
| Presence of White light | NO | NO | YES | YES | NO |

Example 3. Sterilization

Example 2.5 was sterilized under different temperature and time conditions. The table below shows the sterilization temperatures and time conditions:

TABLE 3

| Sterilization conditions. | | | | | | | |
| --- | --- | --- | --- | --- | --- | --- | --- |
| | Ex. 3.1 | Ex. 3.2 | Ex. 3.3 | Ex. 3.4 | Ex. 3.5 | Ex. 3.6 | Ex. 3.7 |
| Temperature (° C.) | 110 | 118 | 121 | 121 | 121 | 121 | 125 |
| Time (min) | 35 | 30 | 15 | 20 | 25 | 35 | 6 |

Example 4. Comparative Example: Impurities

Total impurities and highest unknown impurity G (relative retention time, RRT 0.17) were determined by HPLC (High Performance Liquid Chromatography).

TABLE 4

Unknown impurity G and total impurity content of examples and Bridion ®.

| Sample | Unknown Impurity G (% w/w) | Total impurities (% w/w) |
| --- | --- | --- |
| Ex. 2.1 | 0.11 | 1.21 |
| Ex. 2.2 | 0.11 | 1.34 |
| Ex. 2.3 | 0.1 | 1.23 |
| Ex. 2.4 | 0.11 | 1.33 |
| Ex. 2.5 | 0.11 | 0.85 |
| Ex. 3.1 | 0.11 | 0.9 |
| Ex. 3.2 | 0.15 | 1.5 |
| Ex. 3.3 | 0.11 | 1.2 |
| Ex. 3.4 | 0.16 | 0.82 |
| Ex. 3.5 | 0.2 | 1.00 |
| Ex. 3.6 | 0.17 | 1.22 |
| Ex. 3.7 | 0.08 | 1.19 |
| Bridion ® N034416 | 0.31 | 3.8 |
| Bridion ® R000207 | 0.33 | 3.86 |
| Bridion ® N008816 | 0.33 | 3.67 |
| Bridion ® M034113 | 0.27 | 3.4 |

As can be seen in Table 2, aqueous liquid pharmaceutical compositions prepared according to the present invention show a lower level of impurities than Bridion® batches.

The invention claimed is:

1. A method for preparing a sterilized aqueous liquid pharmaceutical composition suitable for intravenous administration comprising an active ingredient and water, wherein the active ingredient consists of sugammadex, a pharmaceutically acceptable salt of sugammadex, or a mixture thereof, wherein the method comprises at least the following steps:
   a) providing an aqueous solution comprising the active ingredient;
   b) optionally, adjusting the pH of the solution obtained in step a) from about 7 to about 8;
   c) filtering the solution obtained in step a), or optionally the solution of step b), through a pore filter that is equal to or less than 0.45 μm to obtain a filtered solution comprising the active ingredient;
   d) filling a suitable pharmaceutical container with the filtered solution obtained in step c);
   e) terminally sterilizing the solution obtained in step d) at a temperature from about 110° C. to about 130° C. for less than about 37 min to obtain the sterilized aqueous liquid pharmaceutical composition suitable for intravenous administration having an individual unknown impurity G amount of less than 0.25% (w/w).

2. The method according to claim 1, wherein step c) is performed at least twice, and least one filtration is through a pore filter that is equal to or less than 0.45 μm pore filter and/or at least one filtration through a pore filter that is equal to or less than 0.3 μm pore filter or a 0.2 μm pore filter.

3. The method according to claim 1, wherein step e) is carried out at a temperature from about 115° C. to about 125° C.

4. The method according to claim 1, wherein step e) is carried out for about 10 min to about 31 min.

5. The method according to claim 1, wherein step e) is carried out at a temperature from about 115° C. to about 125° C., and for about 10 min to about 31 min.

6. The method according to claim 1, wherein the terminal sterilization of step e) is a thermal sterilization.

7. The method according to claim 1, wherein step c) is performed at least once, wherein the sterilization temperature in step e) is from about 115° C. to about 125° C., and the sterilization time in step e) is more than about 15 min.

8. The method according to claim 1, wherein the pH in the aqueous liquid pharmaceutical composition is from about 7.2 to about 7.8.

9. The method according to claim 1, further comprising deoxygenating the solution comprising the active ingredient.

10. The method according to claim 1, wherein the terminal sterilization of step e) is a moist heat sterilization selected from the group consisting of moist heat sterilization and superheated water spray sterilization.

11. The method of claim 1, wherein the aqueous liquid pharmaceutical composition suitable for intravenous administration comprises an effective amount of a pH adjuster to maintain the pH in a range from about 7 to about 8 and wherein the total amount of impurities is less than about 3% (w/w).

12. The method of claim 1, wherein the aqueous liquid pharmaceutical composition suitable for intravenous administration has a pH in a range from about 7.2 to about 7.8.

13. The method of claim 1, wherein the aqueous liquid pharmaceutical composition suitable for intravenous administration has a pH in a range from about 7.4 to about 7.6.

14. The method of claim 1, wherein the aqueous liquid pharmaceutical composition suitable for intravenous administration has a pH of about 7.5.

15. The method of claim 1, wherein the aqueous liquid pharmaceutical composition suitable for intravenous administration has a total amount of impurities less than about 1.5% (w/w).

16. The method of claim 1, wherein the aqueous liquid pharmaceutical composition suitable for intravenous administration has a total amount of impurities less than about 1.3% (w/w).

17. The method of claim 1, wherein the aqueous liquid pharmaceutical composition suitable for intravenous administration has an individual unknown impurity G amount of less than about 0.2% (w/w).

18. The method of claim 1, further comprises packaging the aqueous liquid pharmaceutical composition suitable for intravenous administration in a type I vial with a grey chlorobutyl rubber stopper with a seal.

* * * * *

UNITED STATES PATENT AND TRADEMARK OFFICE
CERTIFICATE OF CORRECTION

PATENT NO. : 11,324,692 B2  
APPLICATION NO. : 16/919856  
DATED : May 10, 2022  
INVENTOR(S) : Luis Gomez Coello and Javier Torrejón Nieto Page 1 of 1

It is certified that error appears in the above-identified patent and that said Letters Patent is hereby corrected as shown below:

On the Title Page

Item (54) and in the Specification, Column 1, Lines 1-3, "METHOD TO PREPARE PHARMACEUTICAL COMPOSITIONS OF SUGGAMADEX" should read ---METHOD TO PREPARE PHARMACEUTICAL COMPOSITIONS OF SUGAMMADEX---

Signed and Sealed this  
Sixteenth Day of August, 2022

Katherine Kelly Vidal  
*Director of the United States Patent and Trademark Office*